United States Patent [19]

Witt

[11] Patent Number: 4,540,663

[45] Date of Patent: Sep. 10, 1985

[54] LIQUEFACTION OF STARCH

[75] Inventor: Paul R. Witt, Muscatine, Iowa

[73] Assignee: Grain Processing Corporation, Muscatine, Iowa

[21] Appl. No.: 496,444

[22] Filed: May 20, 1983

[51] Int. Cl.$^3$ .............................................. C12P 19/14
[52] U.S. Cl. ...................................................... 435/99
[58] Field of Search ................................... 435/99, 203

[56] References Cited

U.S. PATENT DOCUMENTS 3,185,633  5/1965  Krebs ..................................... 435/99
3,551,293 12/1970 Seidman et al. ....................... 435/99
4,235,965 11/1980 Walon .................................... 435/95

OTHER PUBLICATIONS

Pommer, Proc. Conv.—Inst. Brew, (Aust. N.Z. Section), 1982, pp. 85–92.

Godfrey et al., Industrial Enzymology, 1983, pp. 204, 214 and 471.

*Primary Examiner*—Lionel M. Shapiro
*Attorney, Agent, or Firm*—Neuman, Williams, Anderson & Olson

[57] ABSTRACT

Starch liquefaction is accomplished using fungal amylase at a temperature of from about 75° C. to 80° C.

9 Claims, No Drawings

LIQUEFACTION OF STARCH

This invention relates to the liquefaction of starch.

Many manufacturing processes, such as in the brewing of beer, the manufacture of paper and the manufacture of confections and the like, utilize starch usually in the form of an aqueous starch solution. Starch granules are initially insoluble in water, but when heated in water they begin to swell rapidly until they are many times their original size. Upon continued heating, the granules begin to disintegrate and the viscosity of the mixture begins to rapidly increase until it reaches a maximum where a paste is formed. The handling of thick starch pastes in manufacturing procedures presents difficulties. Therefore, it is desirable to treat the starch so as to liquefy the starch and reduce its viscosity. Gelatinized, pasted starch can be liquefied by treatment with acids or enzymes or combinations thereof. Thinning of gelatinized starch pastes with acid is known to produce bitter reversion products, such as gentiobiose, and often results in higher dextrose equivalent values than desired, that is, it often results in greater saccharification than is desired. Thinning or liquefaction of starch can also be accomplished with bacterial alpha-amylase, such as amylase derived from *Bacillus subtillus* or *Bacillus licheniformis*. These bacterial alpha-amylases usually must be activated to achieve good liquefying properties and very frequently activation of the enzymes is accomplished by incorporating calcium in the starch slurry. One difficulty with the use of calcium to activate the alpha-amylase liquefying agents is the fact that the calcium is difficult to remove during product clarification and substantial amounts of calcium may remain in the final product, which is undesirable for some applications. Furthermore, the bacterial amylases which are used to liquefy gelatinized starch require relatively high temperatures for inactivation, such as temperatures in excess of 90° C., and for inactivation the pH of the starch slurry must be adjusted to within a very small range, typically pH 4.0 to 5.0. The heating required to reach the inactivation temperature of the bacterial alpha-amylase often tends to increase the dextrose equivalent value of the starch. Moreover, the acid utilized to adjust the pH to the inactivation range contributes to the salt content of the final starch product, which is again not desired for certain applications.

It is therefore a major object of the present invention to provide for the liquefaction of starch using fungal amylase.

It is another object of the present invention to provide for the liquefaction of starch at substantially neutral pH.

It is a still further object of the present invention to provide for the liquefaction of starch in which liquefaction is achieved without significantly increasing the dextrose equivalent value of the liquefied starch.

It is a still further object of the present invention to provide for the liquefaction of starch which does not require the use of enzyme activating agents such as calcium.

The present invention is based on the unexpected discovery that fungal amylase can be used in a limited temperature range to liquefy starch without significant production of low molecular weight sugars. This discovery is wholly unexpected in view of the starch saccharifying properties of fungal amylase. It is well known that fungal amylase can be used at temperatures less than about 70° C. to liquefy and saccharify starch. Fungal amylase at temperatures in the range of about 50° to 65° C. will rapidly produce sugars from gelatinized, pasted starch. For example, fungal amylase at a dosage of about 0.1% acting on a 30% aqueous starch slurry at a pH of 5.5 to 6.0 and temperatures from about 50° to 65° C. will provide a product having a dextrose equivalent value of 43 or more and 50% maltose in about one hour.

It has now been found that starch can be liquefied by treatment with a fungal amylase at a temperature of from about 75° to 80° C. without significant accompanying saccharification. Thus, in accordance with the present invention a gelatinized (pasted) starch is treated with fungal amylase at a temperature of from about 75° C. to 80° C. to reduce the viscosity of the starch paste to a desired extent. Generally treatment of the starch paste with fungal amylase is carried out for a short period of from about 2 to 15 minutes. The starch solids content of the paste can range from about 10 to 40% and preferably about 20 to 30% by weight. The pH of the starch paste undergoing liquefaction with fungal amylase is not critical and the liquefaction can be conducted over a broad pH range of 5.0 to 8.0. After desired liquefaction is achieved, thermal inactivation of the fungal amylase can be accomplished by heating to a temperature of 85°–87° C. Inactivation of the fungal amylase can also be accomplished by downward adjustment to pH 4.0 and heat treatment at 70° C.

Any fungal amylase, such as Fungamyl, Takamyl, Mycolase, Amylozyme, Amylase P, Rohalase M and the like can be used. These fungal amylases are commercially available from Novo Industries, Miles Laboratories, GB Fermentation Industries, ABMC Food Division, England, Gist Brocades, NW and Rohm GMbH, West Germeny, respectively. These fungal amylases can be used to treat waxy or non-waxy gelatinized cereal or root starches or unrefined or unmilled waxy or non-waxy gelatinized starchy materials such as corn grits, corn flour, rice flour, sorghum flour, cassava chips, whole or debranned wheat, barley and the like.

The following examples further illustrate the invention and the advantages thereof. EXAMPLE 1

Corn starch was gelatinized in a jet cooker to form a gelatinized starch paste having a viscosity of 1100 centipoises. Aqueous slurries of the starch paste at a solids level of 26.5 (dry starch basis) were cooled to temperatures of 75° C., 80° C. and 85° C. Then fungal amylase (Fungamyl) at a level of 0.1% based on starch was added and mixed into each slurry. The treated starch slurries were held at these temperatures for 15 minutes. The results of holding the slurries for 15 minutes at these temperatures were as follows:

| | Temperature | Viscosity (centipoises)* | D.E. |
|---|---|---|---|
| Slurry A | 75° C. | 24 | 5.4 |
| Slurry B | 80° C. | 28 | |
| Slurry C | 85° C. | >200 | |

*Viscosity measured at 75° C. using Brookfield RV Model C Viscometer.

After holding for 15 minutes at the temperatures above-indicated, slurries were then held at 60° C. for an additional 20 minutes with the following results:

|  | Temperature | Viscosity (centipoises)** | D.E. |
| --- | --- | --- | --- |
| Slurry A | 60° C. | 26 | 9.4 |
| Slurry B | 60° C. | 28 |  |

**Viscosity measured at 60° C. using Brookfield Model C Viscometer.

The above results show that by treating the gelatinized starch with fungal amylase at temperatures of 75° and 80° C., significant reduction in viscosity (liquefaction) is achieved. Moreover, when held at a temperature of 60° C., the dextrose equivalent (D.E.) value of the treated slurry did not increase dramatically as would be expected when treating pasted starch at this temperature with fungal amylase.

EXAMPLE 2

Jet-cooked (pasted) degermed corn flour (30% dry starch basis), was cooled to 95° C. and 0.1% (by weight of starch) bacterial amylase (Thermamil) added. The bacterial amylase was stirred into the mixture which was held at 95° C. for 15 minutes. The dextrose equivalent value of the treated material at this time was 1. This treatment constituted Step 1. The mixture was then cooled to 75° C. and an aliquot of the treated corn starch was taken. Then, in Step 2, 0.1% fungal amylase (Fungamyl) was mixed with the aliquot and this mixture held at 75° C. for 15 minutes. The results of treatment were:

| Treatment During | Step 1 | | Step 2 | |
| --- | --- | --- | --- | --- |
| Step 2 | centipoises* | DE | centipoises* | DE |
| 75° C. 0.1% Fungal | 74 | 2.4 | 30 | 11.2 |
| 75° C. no amylase | 78 | — | 68 | — |

*Viscosity measured at 60° C. using Brookfield Model C Viscometer.

These results show the significant supplemental liquefaction obtained when bacterial amylase pre-thinned corn flour was additionally treated with a fungal amylase at 75° C.

EXAMPLE 3

Jet-cooked (pasted) corn flour was cooled to 75° C., then 0.1% fungal amylase (Fungamyl) was added and the mixture held at 75° C. for 15 minutes. The viscosity of the jet-cooked corn flour before treatment with fungal amylase was 1200 centipoises at 75° C.

The above was repeated, using 0.1% bacterial amylase (Thermamil) in place of fungal amylase.

Analysis of the two treated mixtures after 15 minutes showed:

| Treatment | Viscosity (centipoises)* | DE |
| --- | --- | --- |
| 0.1% Fungal amylase | 44 | 10.9 |
| 0.1% Bacterial amylase | 108 | — |

*Viscosity measured at 75° C. using Brookfield Model C Viscometer.

After treatment for 15 minutes at 75° C., the corn flour slurries were held for an additional 20 minutes at 60° C. and then analyzed as follows:

| Treatment | Viscosity (centipoises)** | DE |
| --- | --- | --- |
| 0.1% Fungal amylase | 24 | 12.8 |
| 0.1% Bacterial amylase | 92 | — |

**Viscosity measured at 60° C. using Brookfield Model C Viscometer.

The above data show greater liquefaction of corn flour with fungal amylase as compared to bacterial amylase.

EXAMPLE 4

Jet-cooked (pasted) starch slurries (26.5% by weight dry starch basis) at pH 5.6, were cooled to various temperatures in the range 75°–55° C., then 0.1% (by weight starch) fungal amylase (Fungamyl) added. The starch slurries had a viscosity of 1100 centipoises before treatment with fungal amylase. The slurries were held at the various temperatures for 15 minutes and the viscosity determined (viscometer temperature: 60° C.) Then the slurries were held an additional 20 minutes at 60° C. The results were as follows:

| Temperature of Paste When Enzyme Added °C. | Viscosity of Paste After Held 15 Minutes At Temperature of Test Centipoises | DE of Paste After 15 Minutes at Temperature of Test Plus an Additional 20 Minutes at 60° C. DE |
| --- | --- | --- |
| 75 | 26 | 9 |
| 70 | 24 | 12 |
| 65 | 18 | 32 |
| 60 | 16 | not run |
| 55 | not run | 40 |

These data show the substantial decrease in saccharification at a temperature of 75° C. as compared with 55° C.

EXAMPLE 5

Gelatinized corn starch was treated with hydrochloric acid to a viscosity of 60 centipoises at 75° C. The acid thinned starch in water at a starch level of about 23% solids was treated at a pH of 6.8 to 7.0 with fungal amylase (Fungamyl) at levels of 0.1% and 0.2% based on weight of starch for 15 minutes and 30 minutes at 75° C. A sample of the acid thinned starch to which no fungal amylase was added was utilized as a control. The following results were obtained with viscosity readings being taken at 75° C.

|  | Reaction time (minutes) at 75° C. | | | |
| --- | --- | --- | --- | --- |
|  | 15 | | 30 | |
| Treatment | Viscosity, cp | DE | Viscosity, cp | DE |
| 0.1% Fungamyl | 26 | 6.2 | 23 | 6.7 |
| 0.2% Fungamyl | 24 | 6.6 | 20 | 6.8 |
| Control (no enzyme) | 57 | 2.4 | 52 | 2.5 |

The above data show the starch thinning effect of fungal amylase on starch pre-thinned with acid.

EXAMPLE 6

A suspension of starch in water (30% dry starch basis) was heated to 60° C. and then treated with 0.1% by weight of starch bacterial amylase (Thermamil). The mixture was held at 95° C. for 15 minutes. A sample resulting from this treatment (Step 1) was withdrawn. The mixture was then cooled to 75° C., and 0.1% fungal amylase added and the mixture held at 75° C. for 15 minutes. A sample was taken at the end of this 15-minute period (Step 2). The mixture was next cooled to and held at 60° C. for 15 minutes. A third sample was taken at this point (Step 3).

Two additional runs were made as described above, except that the second step (Step 2) was modified to permit enzyme reaction at temperatures of 80° C. and 85° C. respectively.

Two additional runs were made using 0.1% bacterial amylase (Thermamil) in Step 2. This bacterial amylase treatment was in addition to the initial 0.1% bacterial amylase added at the beginning of each run. The results of these runs are shown below:

| | | Treatment in Step 2 | | | | | |
|---|---|---|---|---|---|---|---|
| | | Step Viscometer 1 | | Step #2 | | Step #3 | |
| Temp. °C. | Type of Amylase 0.1% | Viscosity,* (centipoises) | DE | Viscosity,* (centipoises) | DE | Viscosity,* (centipoises) | DE |
| 75 | fungal | 98 | 6.4 | 45 | 17.5 | 38 | 22.9 |
| 80 | fungal | 98 | 6.4 | 45 | 9.2 | 36 | 12.8 |
| 85 | fungal | 98 | 6.4 | 70 | 8.2 | 68 | 8.8 |
| 75 | bacterial | 95 | 6.0 | 56 | 9.4 | 52 | 10.9 |
| 80 | bacterial | 95 | 6.0 | 54 | 9.2 | 52 | 11.5 |

*Viscosity measured at 75° C. using Brookfield Model C Viscometer.

The data show that fungal amylase, acting at 75° C. or 80° C. on bacterial amylase pre-thinned starch results in lower viscosities than when the substrate is treated with additional bacterial amylase.

EXAMPLE 7

Gelatinized starch exiting from a jet-cooker at 26.5% dry starch basis (dsb) was cooled to 95° C. and then treated with 0.1% of the bacterial amylase, Thermamil. The bacterial amylase was stirred into the paste and the mixture held at 95° C. for 15 minutes. This constituted Step 1. A sample was withdrawn for viscosity and dextrose equivalent measurement.

The mixture was then cooled to 75° C. In one run the mixture was treated at this point with 0.1% of the fungal amylase, Fungamyl. In a second run, no fungal amylase was added. In both runs the mixture was held during this step (Step 2) at 75° C. for 15 minutes. Again a sample was withdrawn from each run for analyses. Each mixture was then cooled to 60° C. and held there for 20 minutes (Step 3) before the final samples were taken. Viscosity readings of samples from Steps 1 and 2 were made with the solutions at 75° C. The viscosity after Step 3 was read at 60°. The results were as follows:

| | Run | | | |
|---|---|---|---|---|
| | 1 0.1% Bacterial Amylase 95° 0.1% Fungal Amylase 75° | | 2 0.1% Bacterial Amylase No Fungal Amylase | |
| | Viscosity (centipoises) | DE | Viscosity (centipoises) | DE |
| Step 1 | 12 | 8.5 | 12 | 8.5 |
| Step 2 | 14 | 16.2 | 15 | not run |
| Step 3 | 16 | 20.6 | 18 | 19.8 |

The data show that when jet cooked starch is pre-thinned with bacterial alpha-amylase, very little additional thinning is accomplished by treatment with fungal amylase. Presumably, this is due to the fact that jet cooking of the starch together with bacterial alpha-amylase thinning afford a maximum degree of liquefaction. In such case, the use of fungal amylase is not necessary.

The advantages of the invention are readily apparent. Pure starch pastes or pastes formed from unrefined or dry milled starchy materials can be readily liquefied without the use of activating agents. Relatively low temperatures are suitable for inactivation of the fungal amylase and inactivation of the fungal amylase does not require the use of acids to lower the pH. Liquefaction of the starch is achieved without a significant increase in saccharification and the present liquefaction process has wide applicability. Fungal amylase can be used alone to effect starch liquefaction or can be used to extend liquefaction of starch pastes cooked at atmospheric pressure (not jet cooked) which are pre-thinned by the use of acid or enzymes.

Those modifications and equivalents which fall within the spirit of the invention are to be considered a part thereof.

What is claimed is:

1. A process of treating a starch paste which comprises treating a starch paste with a fungal amylase at a temperature in the range of from about 75° C. to 80° C. for a period sufficient to effect reduction of the viscosity of the starch paste without significant increase in the dextrose equivalent value of the paste.

2. A process in accordance with claim 1 wherein after accomplishment of viscosity reduction to a desired extent, the fungal amylase is thermally inactivated.

3. A process in accordance with claim 1 wherein the treatment with fungal amylase is conducted at a pH of from about 5.0 to 8.0.

4. A process in accordance with claim 1 wherein the starch paste treated is a substantially pure starch paste.

5. A process in accordance with claim 2 wherein the starch paste treated is a substantially pure starch paste.

6. A process in accordance with claim 3 wherein the starch paste treates is a substantially pure starch paste.

7. A process in accordance with claim 1 wherein the starch paste treated is produced from an unrefined or dry milled starchy material.

8. A process in accordance with claim 2 wherein the starch paste treated is produced from an unrefined or dry milled starchy material.

9. A process in accordance with claim 3 wherein the starch paste treated is produced from an unrefined or dry milled starchy material.

* * * * *